(12) United States Patent
Sugita

(10) Patent No.: US 8,052,682 B2
(45) Date of Patent: Nov. 8, 2011

(54) HIGH-FREQUENCY INCISION INSTRUMENT FOR ENDOSCOPE

(75) Inventor: Noriyuki Sugita, Saitama (JP)

(73) Assignee: Hoya Corporation, Tokyo (JP)

( * ) Notice: Subject to any disclaimer, the term of this patent is extended or adjusted under 35 U.S.C. 154(b) by 917 days.

(21) Appl. No.: 11/550,508

(22) Filed: Oct. 18, 2006

(65) Prior Publication Data

US 2007/0088353 A1  Apr. 19, 2007

(30) Foreign Application Priority Data

Oct. 19, 2005  (JP) ................ P2005-303891

(51) Int. Cl.
  *A61B 18/14* (2006.01)
(52) U.S. Cl. .................................................. 606/46
(58) Field of Classification Search .......... 606/46
  See application file for complete search history.

(56) References Cited

U.S. PATENT DOCUMENTS

| | | | | |
|---|---|---|---|---|
| 4,708,137 A | * | 11/1987 | Tsukagoshi | 606/46 |
| 5,681,276 A | * | 10/1997 | Lundquist | 604/22 |
| 6,004,318 A | * | 12/1999 | Garito et al. | 606/41 |
| 6,090,107 A | * | 7/2000 | Borgmeier et al. | 606/41 |
| 6,829,508 B2 | * | 12/2004 | Schulman et al. | 607/116 |
| 7,367,974 B2 | * | 5/2008 | Haemmerich et al. | 606/41 |
| 2003/0060842 A1 | | 3/2003 | Chin et al. | |
| 2005/0090728 A1 | * | 4/2005 | Mest | 600/373 |
| 2005/0215853 A1 | | 9/2005 | Ouchi | |
| 2006/0155271 A1 | | 7/2006 | Sugita et al. | |
| 2006/0178656 A1 | | 8/2006 | Sugita et al. | |
| 2006/0178657 A1 | | 8/2006 | Sugita et al. | |
| 2006/0178669 A1 | | 8/2006 | Sugita et al. | |
| 2009/0005637 A1 | | 1/2009 | Chin et al. | |

FOREIGN PATENT DOCUMENTS

| | | |
|---|---|---|
| JP | 3-015081 | 4/1991 |
| JP | 5-042166 | 2/1993 |
| JP | 6-013741 | 4/1994 |
| JP | 8-299355 | 11/1996 |
| JP | 2000-037455 | 2/2000 |
| JP | 2002-113016 | 4/2002 |
| JP | 2004-016504 | 1/2004 |
| JP | 2005-503863 | 2/2005 |

(Continued)

OTHER PUBLICATIONS

English Language Abstract of JP 2000-037455.

(Continued)

*Primary Examiner* — Lee Cohen
(74) *Attorney, Agent, or Firm* — Greenblum & Bernstein, P.L.C.

(57) ABSTRACT

A high-frequency incision instrument for an endoscope is provided with a flexible sheath, and a rod electrode remotely operated to protrude from/retract into the distal end portion of the sheath. A stationary stopper provided at the distal end portion of the sheath and a movable stopper provided at the proximal end portion of the rod electrode, the movable stopper contacting the stationary stopper to define a maximum protruding amount of the rod electrode from the distal end of the sheath. A proximal end portion of the rod electrode is screw-engaged with a member to which the movable stopper is formed, and the rod electrode is rotatable so that screw-engaged amount of the proximal end portion of the rod electrode with respect to the member is changed, thereby a distance between the tip end of the rod electrode and the movable stopper being adjustable.

6 Claims, 5 Drawing Sheets

FOREIGN PATENT DOCUMENTS

| | | |
|---|---|---|
| JP | 2005-270240 | 10/2005 |
| JP | 2005-279126 | 10/2005 |

OTHER PUBLICATIONS

English Language Abstract of JP 2002-113016.
U.S. Appl. No. 11/550,528 to Sugita, filed Oct. 18, 2006.
Japan Office action that issued with respect to patent family member Japanese Patent Application No. 2005-303891, dated Jan. 26, 2011 along with an english translation thereof.
Japan Office action for corresponding JP Application No. 2005-303891, dated Apr. 6, 2011 along with an english translation thereof.

* cited by examiner

HIGH-FREQUENCY INCISION INSTRUMENT FOR ENDOSCOPE

BACKGROUND OF THE INVENTION

The present invention relates a high-frequency incision instrument for an endoscope. A high-frequency incision instrument for an endoscope is used for incision of in vivo mucosa and the like. The high-frequency incision instrument is generally inserted through an instrument channel of the endoscope. Typically, the high-frequency incision instrument is configured such that a rod electrode provided at a tip end portion of a flexible sheath is operated to protruded forward or retracted from the tip end of the sheath by an operating unit connected to the proximal end of the sheath.

Depth of the incision of the in vivo mucosa depends on a condition of a target portion and/or operational conditions of the high-frequency incision instrument, it is preferable that the depth is adjusted to be safe and optimum amount for the target portion by adjusting a protruding amount of the rod electrode. An example of such a configuration is disclosed in Japanese Patent Provisional Publication No. P2002-113016A (hereinafter, referred to as '016 publication).

According to the invention disclosed in '016 publication, stoppers configured to abut against each other are provided to the tip end of the sheath and the proximal end of the rod electrode, respectively, and a position of a cap member screwed onto the tip end of the sheath is adjusted so that the maximum protruding amount of the rod electrode with respect to the tip end of the sheath is restricted.

When in use, the high-frequency incision instrument is inserted through the instrument channel arranged inside an inserting section of the endoscope. Since the inserting section is bent inside a human cavity, the cap member screwed onto the sheath may be rotated when the high-frequency incision tool is inserted through such an instrument channel, and the adjusted condition of the protruding amount of the rod electrode may be changed. In the worst case, the cap may be disengaged from the sheath inside the human cavity.

SUMMARY OF THE INVENTION

Aspects of the invention provide an improved high-frequency incision instrument for an endoscope which is configured such that the maximum projecting amount of the rod electrode is adjustable, and the adjusted amount will not be changed when the instrument is inserted through the instrument channel and no members of the instrument will not detached from the instrument inside the human cavity.

According to aspects of the invention, there is provided a high-frequency incision instrument for an endoscope, which is provided with a flexible sheath, a rod electrode arranged at a distal end portion of the sheath, the rod electrode being remotely operated to protrude from/retract into the distal end portion of the sheath by an operation of an operating unit which is connected to a proximal end of the sheath, a stationary stopper provided at the distal end portion of the sheath and a movable stopper provided at the proximal end portion of the rod electrode, the movable stopper contacting the stationary stopper to define a maximum protruding amount of the rod electrode from the distal end of the sheath. A proximal end portion of the rod electrode is screw-engaged with a member to which the movable stopper is formed, the rod electrode being rotatable from outside the sheath about the axis of the rod electrode so that screw-engaged amount of the proximal end portion of the rod electrode with respect to the member to which the movable stopper is formed is changed, a distance between the tip end of the rod electrode and the movable stopper being adjustable by rotating the rod electrode.

The tip end of the rod electrode can be retracted in the distal end portion of the sheath irrespective of the distance between the tip end of the rod electrode with respect to the movable stopper when the operation unit is operated to retract the rod electrode inside the distal end portion of the sheath.

The graduations are formed on the outer surface of the rod electrode to indicate a protruding amount of the rod electrode with respect to the distal end of the sheath.

The member to which the movable stopper is formed may be connected with an operation wire. The operation unit moves forward/backward the operation wire to protrude/retract the rod electrode from/to the distal end portion of the sheath.

The member to which the movable stopper is formed may be made of electrically conductive material, a high-frequency current is supplied to the rod electrode via the operation wire and the member to which the movable stopper is formed.

BRIEF DESCRIPTION OF THE ACCPMPANYING DRAWINGS

Figure 3:
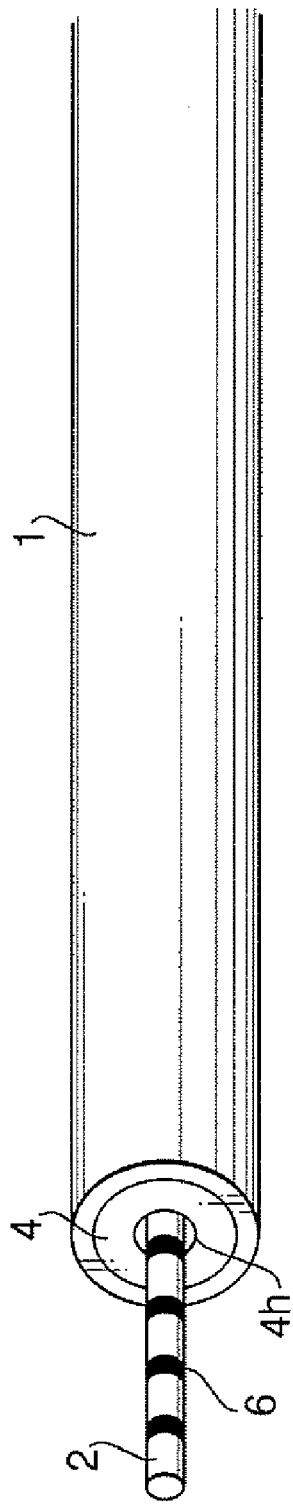
Figure 4:
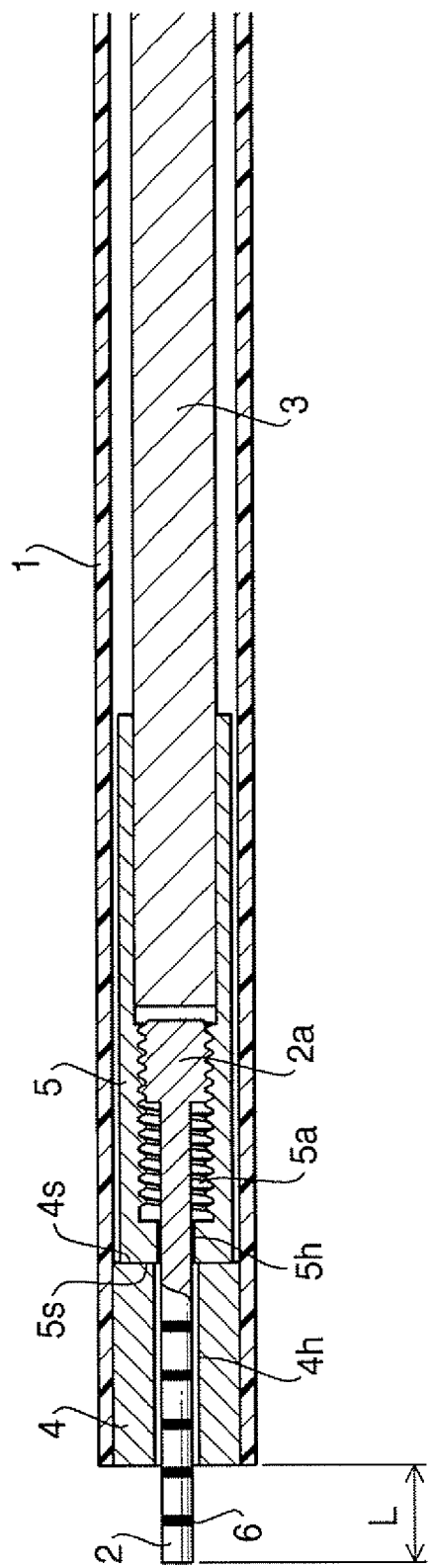
Figure 5:
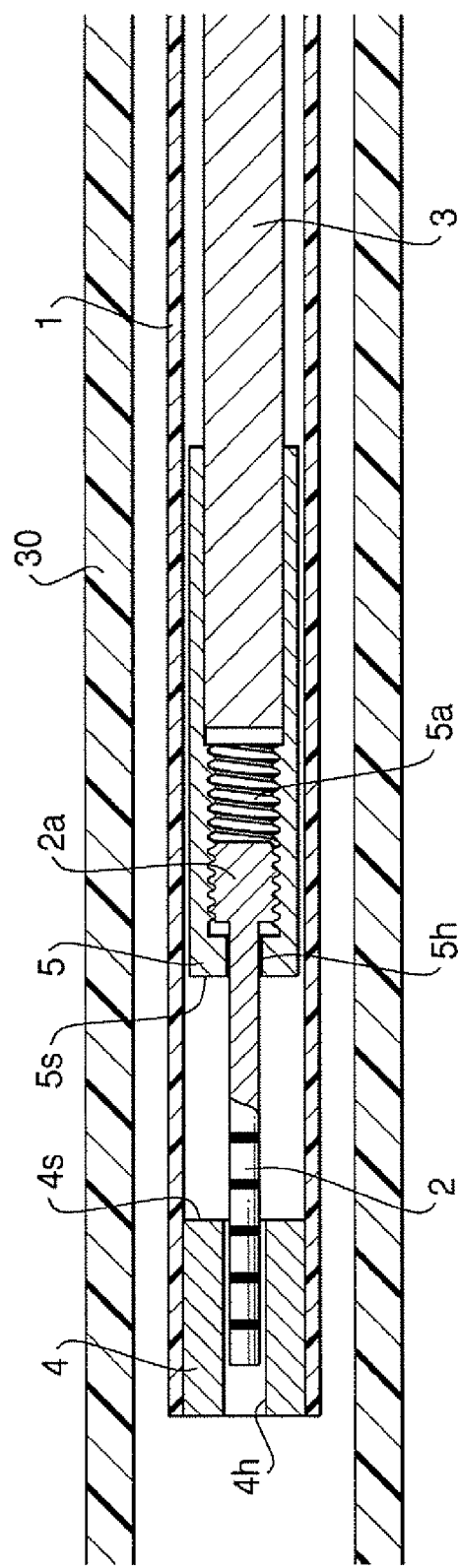

FIG. 3 is a perspective view of the tip portion of the high-frequency incision instrument according to the embodiment of the invention FIG. 4 a cross sectional side view of the tip portion of the high-frequency incision instrument in which a maximum protruding amount of a rod electrode is decreased FIG. 5 shows a cross sectional side view of the tip portion of the high-frequency incision tool inserted through an instrument channel of an endoscope.

DETAILED DESCRIPTION OF THE EMBODIMENT

Hereinafter, referring to accompanying drawings, aspects of the invention will be described.

Figure 2:
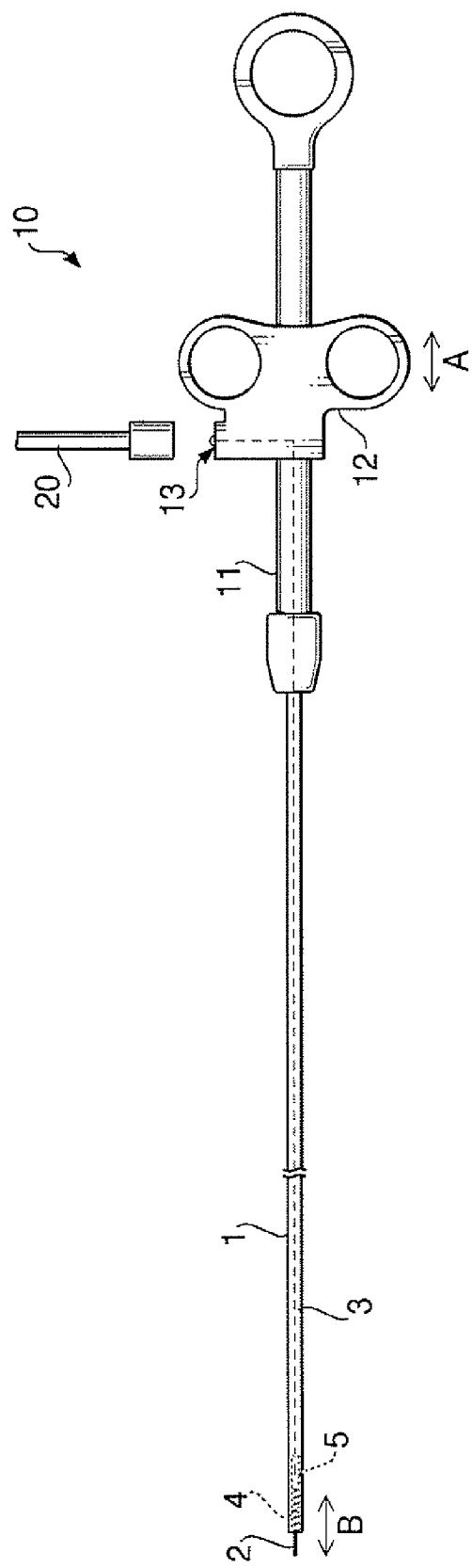
FIG. 2 is a side view showing an entire structure of the high-frequency incision instrument according to the embodiment of the invention.

FIG. 2 shows an entire structure of a high-frequency incision instrument for an endoscope according to an embodiment of the invention. The high-frequency incision instrument is provided with a sheath 1 which is inserted through an instrument channel of an endoscope (not shown). The sheath 1 is a tubular member made of electrically insulating material such as ethylene tetrafluoride. At the tip of the sheath 1, an electrically conductive rod terminal 2 is provided so as to protrude forward from or retracted into the sheath 1.

Inside the sheath 1, an electrically conductive operation wire 3, which is connected to the rod terminal 2, is inserted over an entire length of the sheath 1 such that the operation wire 3 is movable in an axial direction. An operation unit 10 for operating the operation wire 3 to move forward/backward is provided at the proximal end of the sheath 1.

In the operation unit 10, a slide operating member 12, which is slidable with respect to the operation unit main body 11 having a straightly elongated shape extending in the axial direction is provided. To the slide operating member 12, the proximal end of the operation wire 3 is fixedly connected.

In FIG. 2, 13 denotes a connection terminal arranged in the slide operating member 12 and is electrically connected to the operation wire 3. That is, by connecting a high-frequency power source cord 20 with the connection terminal 13, the high-frequency current can be supplied to the rod terminal 2 via the operation wire 3.

At the operation unit 10 thus constructed, when a user slides the slid operating unit 12 in a direction A indicated by arrow, the rod terminal 2 projects from/retracts in the sheath 1. Stopper members 4 and 5 which regulate the maximum projecting amount of the rod terminal 2 are provided at the tip end portion of the sheath 1 and at the proximal end portion of the rod terminal 2.

Figure 1:
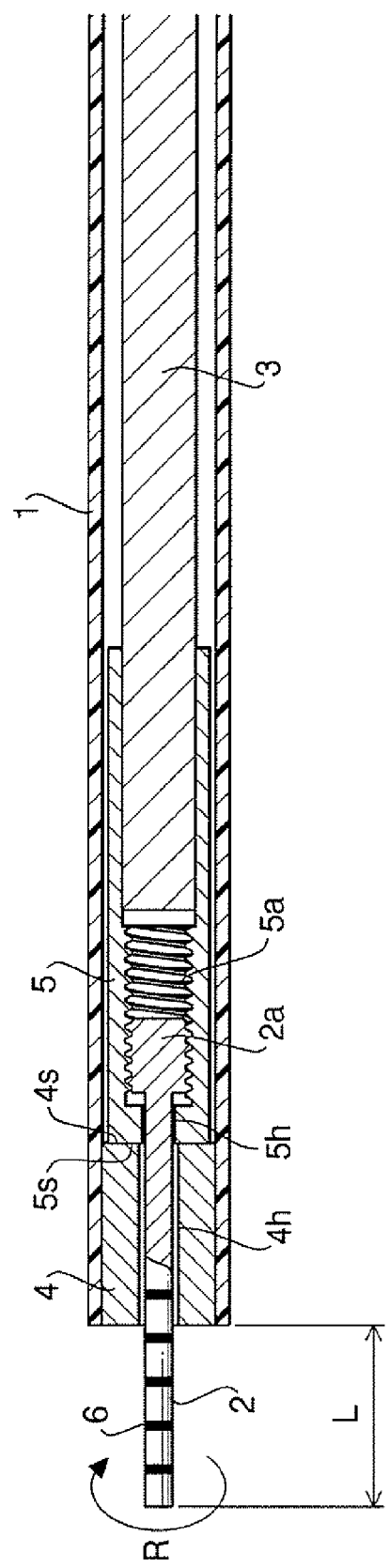
FIG. 1 is a cross sectional side view showing a tip portion of a high-frequency incision instrument for an endoscope according to an embodiment of the invention.

FIG. 1 shows a cross sectional view of the tip portion of the high-frequency incision tool for the endoscope. In this example, a stationary side stopper member 4 is, for example, made of insulating material and formed to have a cylindrical shape, which is firmly fixed at the tip end of the sheath 1. the rod terminal 2, which may be formed as an elongated cylindrical shape is loosely passing through a circular opening 4h formed at an axial position of the stopper member 4.

A movable stopper member 5 is, for example, made of conductive metallic material such as stainless steel having a cylindrical shape, and secured to the tip end of the operation wire 3 by hard soldering or the like. At the tip end of the stopper member 5, an opening 5h through which the rod terminal 2 loosely passes through is formed.

The proximal end of the rod terminal 2 is formed to be a male screw section 2a having a diameter greater than the outer diameter of the rod terminal 2. Further, a female screw section 5a to engage with the male screw section 2a is formed about the axis of the front side half of the movable stopper member 5.

With the above configuration, via the movable stopper member 5, the high frequency current is supplied from the operation wire 3 to the rod terminal 2. It should be noted that the female screw portion 5a of the movable stopper member 5 is formed to be slightly longer (e.g., 1-3 mm) in the axial direction than the male screw section 2a of the rod terminal 2.

On the outer surface of the rod terminal 2, a graduation 6 referred to in order to check the projecting amount of the rod terminal 2 from the tip end of the sheath 1 is formed. Specifically, the graduation includes a mark at every 0.5 mm, for example. Thus, as show in FIG. 3, the number of the marks 6 observed from outside, the protruded length of the rod terminal 2 from the tip end of the sheath 1 can be known.

In the high-frequency incision instrument for endoscope configured as above, when the user operate to push forward the operation wire 3 using the slide operation member 12, the rod terminal 2 is protruded forward from the tip end of the sheath 1. As shown in FIG. 1, the front end surface 5s of the movable stopper member 5 abuts the rear end surface 4s of the stationary stopper member 4, and the rod terminal 2 is prevented from moving forward. The protruding amount of the rod terminal 2 from the tip end of the sheath 1 is the maximum protruded amount L.

Then, if the user pinches the protruded portion of the rod terminal 2 with the fingers, and rotate the same about its axis as shown in FIG. 1 by arrow R, since the male screw section 2a engages with the female screw section 5a of the stopper member 5, the rod terminal 2 moved in the axial direction with respect to the stopper member 5 as shown in FIG. 4, and a distance between the tip end surface 5s of the movable stopper member 5 and the tip end of the rod terminal 2. Thus, the maximum protruded amount L of the rod terminal with respect to the tip end of the sheath 1 can be adjusted.

It should be noted that, irrespective of how long the maximum protruding amount L is, when the user operates to pull the operation wire 3 using the slide operation member 12 of the operation unit 10, the tip end of the rod terminal 2 is retracted in the tip end portion of the sheath 1 or at least the tip end of the rod terminal 2 is positioned on the same plane of the tip end of the sheath 1 as shown in FIG. 5.

Accordingly, when the sheath 1 is inserted through the instrument inserting channel 30 of the endoscope, irrespective of a bending status of the instrument inserting channel 30, the rod terminal 2 will not contact the inner wall of the instrument inserting channel 30. Thus, the rod terminal 2 will not be rotated when the sheath 1 is inserted through the instrument inserting channel 30. Therefore, the pre-set maximum protruding amount L of the rod terminal 2 will not change unintentionally. Further, the rod terminal 2 may not be removed from the tip end of the sheath 1.

The present disclosure relates to the subject matter contained in Japanese Patent Application No. 2005-303891, filed on Oct. 19, 2005, which is expressly incorporated herein by reference in its entirety.

What is claimed is:

1. A high-frequency incision instrument for an endoscope, comprising:
    a flexible sheath;
    a rod electrode arranged at a distal end portion of the sheath, the rod electrode being remotely operated to move linearly along an axis of the sheath to protrude from/retract into the distal end portion of the sheath by an operation of an operating unit which is connected to a proximal end of the sheath;
    a stationary stopper fixed in the distal end portion of the sheath and a movable stopper provided at a proximal end portion of the rod electrode, the movable stopper contacting the stationary stopper to define a maximum protruding amount of the rod electrode from the distal end portion of the sheath,
    the proximal end portion of the rod electrode being screw-engaged with a member to which the movable stopper is formed, the rod electrode being rotatable by engaging a distal end portion of the rod electrode from outside the distal end portion of the sheath about an axis of the rod electrode to change a screw-engaged amount of the proximal end portion of the rod electrode with respect to the member to which the movable stopper is formed, a distance between a tip end of the rod electrode and the movable stopper being adjustable by rotating the rod electrode by engaging the distal end portion of the rod electrode outside the distal end of the sheath,
    wherein graduations are provided on an outer surface of the rod electrode over an entire extendible length of the rod electrode to indicate a protruding amount of the rod electrode with respect to the distal end of the sheath.

2. The high-frequency incision instrument according to claim 1,
    wherein the tip end of the rod electrode can be retracted in the distal end portion of the sheath irrespective of the distance between the tip end of the rod electrode with respect to the movable stopper when the operation unit is operated to retract the rod electrode inside the distal end portion of the sheath.

3. The high-frequency incision instrument according to claim 1,
    wherein the member to which the movable stopper is formed is connected with an operation wire, the operation unit moving the operation wire forward/backward to protrude/retract the rod electrode from/to the distal end portion of the sheath.

4. The high-frequency incision instrument according to claim 3,
wherein the member to which the movable stopper is formed is made of electrically conductive material, a high-frequency current is supplied to the rod electrode via the operation wire and the member to which the movable stopper is formed.

5. The high-frequency incision instrument according to claim 1, wherein the proximal end portion of the rod electrode includes a male screw that is integrally formed with the rod electrode, and the member to which the movable stopper is formed includes a female screw that engages with the male screw of the rod electrode.

6. The high-frequency incision instrument according to claim 5, wherein the female screw is longer than the male screw.

* * * * *